(12) United States Patent
Roy et al.

(10) Patent No.: US 11,072,808 B2
(45) Date of Patent: Jul. 27, 2021

(54) METHODS AND COMPOSITIONS FOR INCREASING CAPPING EFFICIENCY OF TRANSCRIBED RNA

(71) Applicant: New England Biolabs, Inc., Ipswich, MA (US)

(72) Inventors: Bijoyita Roy, Medford, MA (US); Jennifer Ong, Salem, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 16/151,908

(22) Filed: Oct. 4, 2018

(65) Prior Publication Data

US 2020/0109425 A1 Apr. 9, 2020

(51) Int. Cl.
C12N 9/12 (2006.01)
C12P 19/34 (2006.01)

(52) U.S. Cl.
CPC .................................... *C12P 19/34* (2013.01)

(58) Field of Classification Search
CPC .................................. C12P 19/34; C12N 9/12
See application file for complete search history.

(56) References Cited

U.S. PATENT DOCUMENTS

| | | | |
|---|---|---|---|
| 7,074,596 B2 | 7/2006 | Darzynkiewicz et al. | |
| 8,217,016 B2 | 7/2012 | Hoerr et al. | |
| 8,383,340 B2 | 2/2013 | Ketterer et al. | |
| 8,680,069 B2 | 3/2014 | de Fougerolles et al. | |
| 8,802,438 B2 | 8/2014 | Rossi et al. | |
| 9,181,321 B2 | 11/2015 | Heartlein et al. | |
| 9,220,792 B2 | 12/2015 | Chakraborty et al. | |
| 9,233,141 B2 | 1/2016 | Chakraborty et al. | |
| 9,371,544 B2 | 6/2016 | Dahl et al. | |
| 9,428,535 B2 | 8/2016 | de Fougerolles et al. | |
| 9,587,003 B2 | 3/2017 | Bancel et al. | |
| 9,597,413 B2 | 3/2017 | Guild et al. | |
| 9,629,804 B2 | 4/2017 | Heartlein et al. | |
| 10,034,951 B1 | 7/2018 | Roy et al. | |
| 10,519,431 B2 * | 12/2019 | Ong ..................... | C12Q 1/6858 |
| 2011/0143436 A1 | 6/2011 | Dahl et al. | |
| 2012/0009221 A1 | 1/2012 | Hoerr et al. | |
| 2012/0251618 A1 | 10/2012 | Schrum et al. | |
| 2012/0258176 A1 | 10/2012 | Sung et al. | |
| 2013/0202645 A1 | 8/2013 | Barner et al. | |
| 2014/0152211 A1 | 6/2014 | Ko | |
| 2016/0032316 A1 | 2/2016 | Weissman et al. | |
| 2016/0038432 A1 | 2/2016 | DeRosa et al. | |
| 2017/0119740 A1 | 5/2017 | Beachy et al. | |
| 2017/0247670 A1 | 8/2017 | Ong et al. | |
| 2018/0105551 A1 | 4/2018 | Chivukula et al. | |
| 2019/0002851 A1 | 1/2019 | Miller et al. | |

FOREIGN PATENT DOCUMENTS

| | | |
|---|---|---|
| WO | 2009077134 A2 | 6/2009 |
| WO | 2009149253 A2 | 12/2009 |
| WO | 2013151666 A2 | 10/2013 |
| WO | 2014152673 A1 | 9/2014 |
| WO | 2016090262 A1 | 6/2016 |

OTHER PUBLICATIONS

Ramanathan et al., Nucleic Acids Research, 44, 7511-7526, 2016.
Muttach, et al., J. Org Chem. 13: 2819-2832, 2017.
Sahin, et al., Nature Reviews Drug Discovery, 13, 759-80, 2014.
Kore, 2006, Nucleotides, Nucleotides, and Nucleic Acids, 25: 337-40.
Ishikawa, et al., Nucleic Acid Symp. Ser., 2009 53:129-30.
Strenkowska, et al., (2016), Nucleic Acids Research, 44(20):9578-90.
Kore, Nucleotides, Nucleotides, and Nucleic Acids, 2006, 25: 307-14.
Beharry, et al., Chemical Society Reviews 2011, 40(8): 4422-37.
Deleavey, et al. Chemistry & Biology 2012, 19(8): 937-54.
Jemielity, et al., 2003, Novel "anti-reverse" cap analogs with superior translational properties. RNA 9:1108-1122.
Kore, et al., 2008, Synthesis and biological evaluation of trimethyl-substituted cap analogs. Bioorg Med Chem Lett 18(3):880-884.
Sikorski, et al., 2020, The identity and methylation status of the first transcribed nucleotide in eukaryotic mRNA 5' cap modulates protein expression in living cells. Nucleic Acid Res 48(4):1607-1626.
Warren, et al., 2010, Highly Efficient Reproogramming to Pluripotency and Directed Differentiation of Human Cells with Synthetic Modified mRNA. Cell Stem Cell 7:618-630.
Steinle, et al., Concise Review: Application of In Vitro Transcribed Messenger RNA for Cellular Engineering and Reprogramming: Progress and Challenges. Stem Cells, 35:68-79.
Hadas, et al., Molecular Therapy, Methods & Clinical Development, 14, 300-305, 2019.
Chamberlin, et al., The Journal of Biological Chemistry, 248, 6, 2235-2244, 1973.

* cited by examiner

*Primary Examiner* — Richard G Hutson
(74) *Attorney, Agent, or Firm* — New England Biolabs, Inc

(57) ABSTRACT

Methods and compositions for capping RNA in an in vitro transcription mixture are provided that include a thermostable RNA polymerase variant and a cap analog such that when a DNA template is added to the mixture, and the mixture is then incubated under conditions for in vitro transcription, capped RNA is produced.

20 Claims, 5 Drawing Sheets

Specification includes a Sequence Listing.

FIG. 2A — WT-T7 (37°C) — Capping efficiency: 92% (1) + (2)

FIG. 2B — M20 (37°C) — Capping efficiency: 100% (1)

FIG. 2C — M20 (50°C) — Capping efficiency: 100% (1)

TAATACGACTCACTATA $A_{+1}G_{+2}G_{+3}$------$N_{25}$
(SEQ ID NO:2)

$\xrightarrow{(1)}$ $m^7G\text{-ppp-}A_{+1}G_{+2}G_{+3}$------$N_{25}$ $\xrightarrow{(2)}$ $\text{ppp-}A_{+1}G_{+2}G_{+3}$------$N_{25}$

FIG. 3A

| Polymerase | Temperature | Capping efficiency [Intensity of Cap-RNA peaks)/ {(Intensity of Cap-RNA peak) + (Intensity of the ppp-RNA peaks)} | | | |
|---|---|---|---|---|---|
| Wild-type T7 RNA polymerase | 37°C | 91% | 89% | 92% | Average: 90.6% |
| Toyobo (polymerase variant) | 37°C | 86.2% | 88.3% | 87.1% | Average: 87.2 |
| Toyobo (polymerase variant) | 50°C | 73.3% | 85.2% | 85.3% | Average: 81.2% |

TAATACGACTCACTATA A$_{+1}$G$_{+2}$G$_{+3}$----------N$_{25}$ → m$^7$G-ppp-A$_{+1}$ G$_{+2}$ G$_{+3}$----------N$_{25}$ (SEQ ID NO:2)

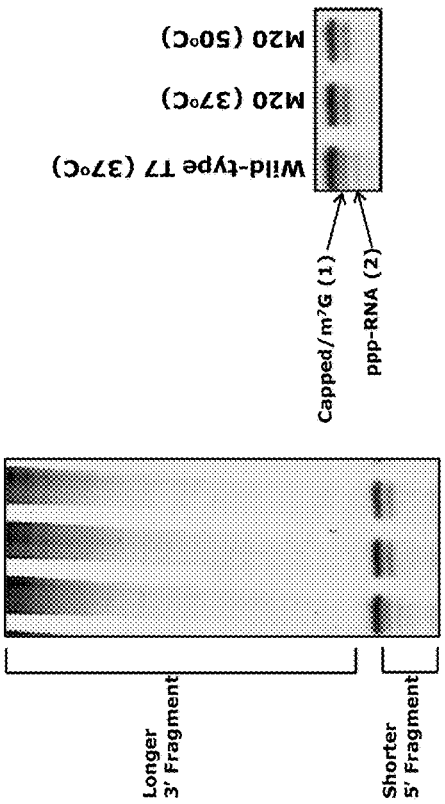
FIG. 4A
FIG. 4B
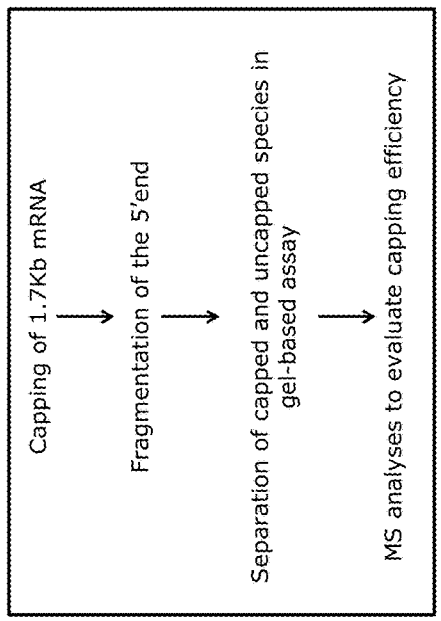
FIG. 4C
| Polymerase used | Temperature used | Capping efficiency intensity of Cap-RNA peaks)/ ((intensity of Cap-RNA peak) + (intensity of the ppp-RNA peaks)) |
|---|---|---|
| Wild-type RNA polymerase | 37°C | 91% |
| M20 (polymerase variant) | 37°C | 99.9% |
| M20 (polymerase variant) | 50°C | 99.8% |

METHODS AND COMPOSITIONS FOR INCREASING CAPPING EFFICIENCY OF TRANSCRIBED RNA

BACKGROUND

Eukaryotic mRNAs have a cap structure at their 5'-termini. The cap consists of 7-methylguanosine ($m^7G$) and a triphosphate bridge, ppp (p3), linking the 5'OH of $m^7G$ to the 5'OH of the 5'-terminal nucleotide, N, denoted $m^7G(5')$pppN ($m^7G(5')$p3N) (Cap 0 structure). The cap structure imparts various biological functions to the capped RNA (Ramanathan et al., (2016) Nucleic Acids Research, 44, 7511-7526). These include mRNA processing and transport; imparting stability to the mRNA molecule; increasing translation efficiency; and acceleration of multiple interactions between the mRNA and the cellular machinery including the translation apparatus, immune receptors and effectors.

RNA synthesized via in vitro transcription (IVT) can be capped during the transcription reaction (in a process called "co-transcriptional capping") or afterwards (i.e., post-transcriptionally using a series of enzymatic steps) (see, e.g., Muttach et al., J. Org Chem. (2017) 13: 2819-2832). In co-transcriptional capping, a cap analog is included in the IVT reaction along with the four ribonucleotide triphosphates. Cap analogs are synthetic analogs of the $N^7$-methylated guanosine triphosphate cap and can add a natural or unnatural cap to the RNA (see Muttach, supra). Co-transcriptional capping methods are limited, however, because the cap analogue competes with GTP as initiator nucleotide in the reaction and, as such, not all mRNA obtained from such IVT is capped. This problem can be mitigated in part using an optimized ratio of cap analog to GTP (i.e., by lowering the GTP concentration) or by digesting uncapped (i.e., triphosphorylated) RNA with a phosphatase which dephosphorylates the 5' end of the RNA (see Muttach, supra). However, the former solution decreases the overall efficiency of the reaction and the latter solution adds work. As such, neither method solves the problem in a practical way and consequently producing large quantities of homogenously capped RNA remains technically challenging.

Therefore, there is still a need for a way to efficiently produce homogenously capped RNA by co-transcriptional capping.

SUMMARY

In general in one aspect, a method is provided for co-transcriptionally capping of an RNA with a cap analog, where the method includes: (a) combining, a mixture of rNTPs, and/or modified nucleotides, and a cap analog of Formula 1 with an RNA polymerase variant for forming a capped transcript from a DNA template, wherein Formula 1 comprises:

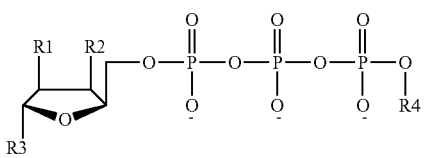

wherein:
$R_1$ and/or $R_2$=O-alkyl, halogen, a linker, hydrogen or a hydroxyl;

$R_3$=guanine, adenine, cytosine, uridine, guanine analog, adenine analog, cytosine analog, uridine analog;

$R_4$=N1-p-N(x), where N=nucleotides or modifications thereof where the nucleotides can include any of adenine, uridine, guanine, or cytidine or analogs of adenine, uridine, guanine, or cytidine bases, and nucleotide modification can be selected from $N^6$-methyladenine, $N^1$-methyladenine, $N^6$-2'-O-dimethyladenosine, pseudouridine, $N^1$-methylpseudouridine, 5-iodouridine, 4-thiouridine, 2-thiouridine, 5-methyluridine, pseudoisocytosine, 5-methoxycytosine, 2-thiocytosine, 5-hydroxycytosine, $N^4$-methylcytosine, 5-hydroxymethylcytosine, hypoxanthine, $N^1$-methylguanine, $O^6$-methylguanine, 1-methyl-guanosine, $N^2$-methyl-guanosine, $N^2,N^2$-dimethyl-guanosine, 2-methyl-2'-O-methyl-guanosine, $N^2,N^2$-dimethyl-2'-O-methyl-guanosine, 1-methyl-2'-O-methyl-guanosine, $N^2,N^2$-dimethyl-2'-O-methyl-guanosine, or isoguanineadenine; wherein:

(i) x can be any integer from 0-8,
  wherein the sugar in the nucleotides may be selected from ribose, arabinose, threonyl furanose, thioribose, deoxyribose, and may comprise one or more modifications including 2'-O-alkyl, 2'-O-methoxyethyl, 2'-O allyl, 2'-O alkylamine, 2'-fluororibose, or 2'-deoxyribose;
  the phosphate groups in one or more nucleotides can be substituted for phosphorothioates, phosphorodithioate, alkyphosphonate, arylphosphonate, or N-phosphoramidate linkages;

(ii) the polynucleotide cap can be a salt or solvated form; and
(iii) the polynucleotide cap can be a single stereoisomer or plurality of stereoisomers of one or more of the compounds described by Formula 1 or a salt or salts thereof; and (b) co-transcriptionally capping the RNA.

In one aspect, the O-alkyl is an O-methyl. In another aspect, Formula 1 is $m^7G$ trinucleotide, such that R3 is 7 methylguanine, R1 and R2 are hydroxyl groups, and x is 1.

In one aspect, the RNA polymerase variant is thermostable. The RNA polymerase variant may include (i) an amino acid sequence is at least 80% sequence identity to SEQ ID NO:1; and (ii) an amino acid substitution at one or more positions corresponding to 388, and 567 of SEQ ID NO:1. More specifically, the RNA polymerase may additionally include an amino acid substitution of at least one position or two or all 4 positions corresponding to positions selected from the group consisting of 109, 205, 534, and 618 of SEQ ID NO:1. More specifically, the RNA polymerase variant may include a mutation or mutations corresponding to D388E and/or V567P. More specifically, the RNA polymerase variant may additionally include an amino acid substitutions at one or more positions or at least 10 positions corresponding to positions selected from the group consisting of: 75, 83, 108, 206, 227, 281, 297, 312, 323, 327, 333, 340, 354, 362, 375, 428, 446, 454, 461, 495, 510, 584, 591, 642, 711, 724, 740, 788, 832, 834, 835, 843, 847, 849, 856, 863, 866 and 877 of SEQ ID NO:1. For example, one or more or ten or more substitutions may include T75Q, A83K, E108L, K206P, V227I, I281P, V297I, Y312D, A323I, A327P, K333P, V340E, A354Q, M362P, T375K, T375N, A428P, L446F, K454P, K461R, S495N, C510Q, A584K, D591E, K642R, K711R, A724P, K740R, G788A, M832F, D834E, T835L, A843Q, D847E, F849V, S856T, A863P, A866K and E877R.

In one aspect, the polymerase variant may be fused to an exogenous DNA binding domain.

In general in one aspect, a kit is provided having a compound according to Formula 1 and an RNA polymerase variant

BRIEF DESCRIPTION OF THE DRAWINGS

The skilled artisan will understand that the drawings described below, are for illustration purposes only. The drawings are not intended to limit the scope of the present teaching in any way.

FIG. 1 shows how conventional co-transcriptional capping methods can result in a mixture of capped products (which have a 5'-m$^7$G -ppp) and uncapped products (which have a 5'-ppp). During the process of IVT, the RNA polymerase binds the promoter sequence in the DNA template (represented in gray) and initiates transcription from the second strand in a 5' direction at a sequence downstream of the promoter represented by the +1 nucleotide in this schematic diagram. The RNA synthesized from this template by the RNA polymerase in the presence of standard nucleotides only has a sequence of ppp-A$_{+1}$G$_{+2}$ ... (rest of the RNA). When the RNA is synthesized from this template by the RNA polymerase in the presence of the trinucleotide cap and standard nucleotides, the RNA transcript should have a 5' sequence of m$^7$G -A$_{+}$1G$_{+}$2 ... (rest of the RNA). However, commercial T7 RNA polymerases provide inefficient 5' m$^7$G incorporation resulting in a heterogeneous population of transcripts where some of the RNA transcripts are capped with 5' m$^7$GAG and some are uncapped 5'-ppp-AG.

FIG. 2A-2D shows chromatograms from liquid chromatography-mass spectrometry (LC-MS) analyses of capped synthetic RNA molecules created by transcription of a 25 base pair template with promoter sequence of (SEQ ID NO:2) TAATACGACTCACTATA-A$_{+1}$G$_{+2}$G$_{+3}$ ... N$_{+25}$. Wild-type T7 RNA polymerase (WT-T7) was used for transcription at 37° C. and a variant of WT-T7 (M20) was used for transcription at 37° C. and 50° C. The transcription product was a 25-mer RNA that was capped (Cap-RNA) or if capping was incomplete, phosphorylated (ppp-RNA).

The X-axis denotes the mass of the RNA products detected and Y-axis denotes the intensity of each RNA species. Capping efficiency was measured using the following formula: (intensity of capped peaks)/[(intensity of capped peaks)+(intensity of the ppp peaks)].

This data shows that the thermostable polymerase M20, which is a thermostable variant of T7 RNA polymerase that is characterized by amino acid substitutions at positions corresponding to 388 and 567 of the WT-T7 sequence among other mutations (see, e.g., U.S. patent application Ser. No. 15/594,090, which is incorporated by reference herein) initiates transcription using a cap analog with 100% efficiency at 37° C. and 50° C., as opposed to the WT-T7 polymerase, which initiates transcription using a cap analog with only 92% efficiency.

FIG. 2A shows the capping efficiency using WT-T7 (reaction temperature 37° C.) where peaks were observed corresponding to capped RNA and also to phosphorylated uncapped RNA. 92% of the RNA was capped and 8% was phosphorylated. Several peaks are shown for capped transcripts because of the know phenomenon of addition of a single nucleotide at the 3' end. Here a 26$^{th}$ nucleotide may be added at the 3' end of the 25-nucleotide transcript to generate two additional peaks corresponding to an addition of C or an addition of G.

FIG. 2B shows the capping efficiency of using M20-T7 RNA polymerase (reaction temperature 37° C.) where peaks were observed corresponding to capped RNA only and none to phosphorylated uncapped RNA. 100% of the RNA was capped.

FIG. 2C shows the capping efficiency of using M20-T7 RNA polymerase (reaction temperature 50° C.) where peaks were observed corresponding to capped RNA only and none to phosphorylated uncapped RNA. 100% of the RNA was capped.

Figure 1:
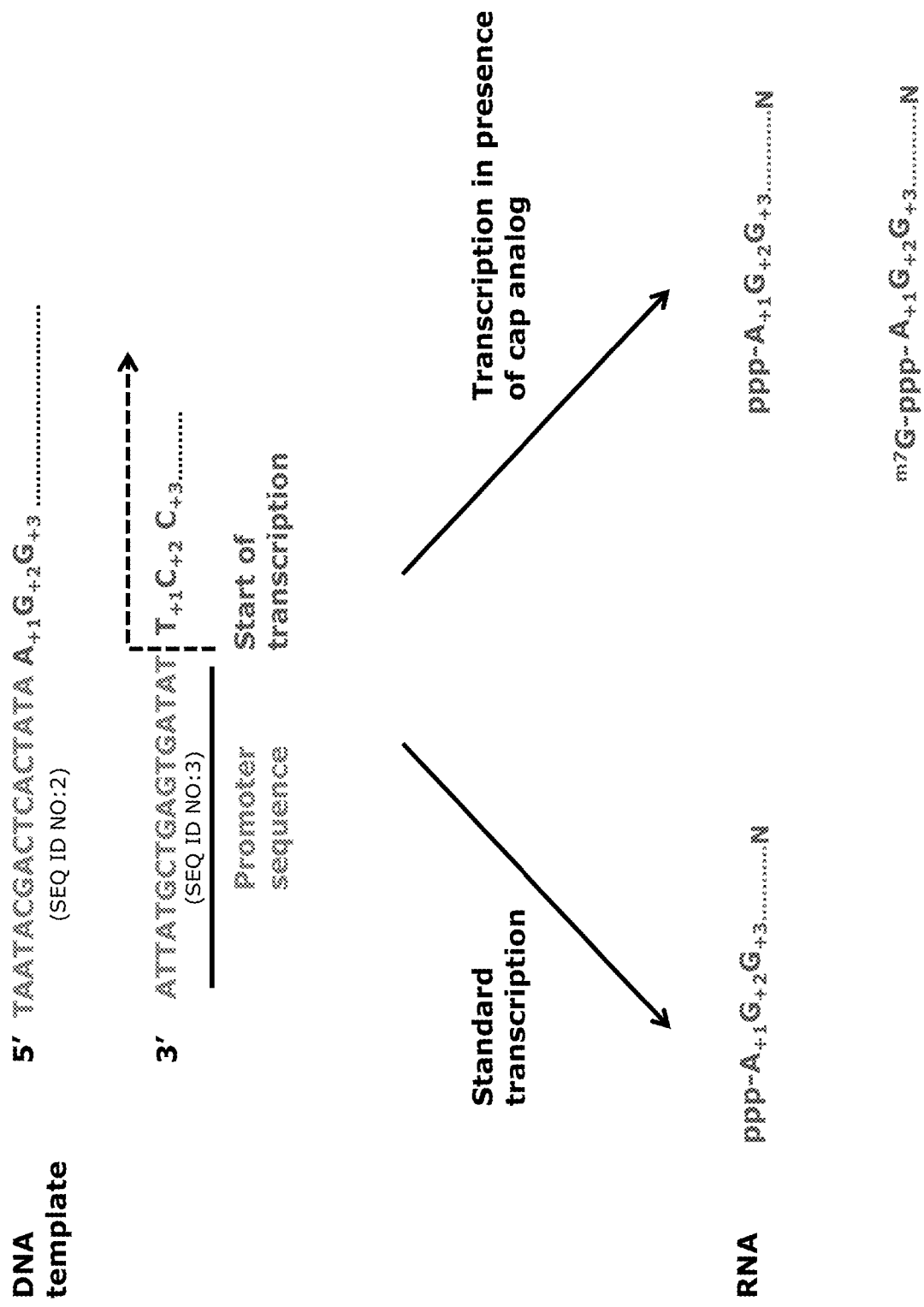
FIG. 1 schematically illustrates how transcription is initiated from a DNA template showing one of the two promoters recognized by T7RNA polymerase. These are duplexes having a 5' TAATACGACTCACTATA (SEQ ID NO:2) sequence (used in FIGS. 1, 2D, 3A, 3B) and the Class II promoter sequence 5' TAATACGACTCACTATT (SEQ ID NO:4) (used in FIG. 3C).
Figure 2D:
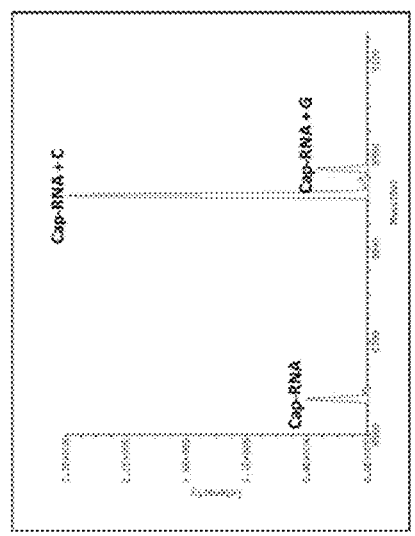
Figure 2D:
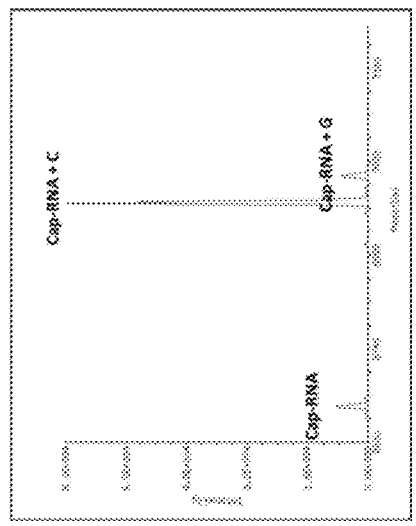
Figure 2D:
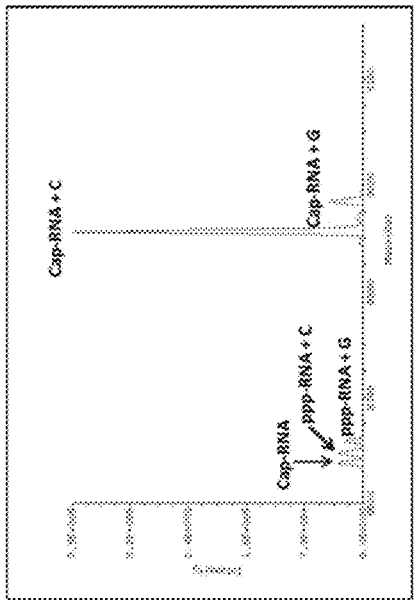
Figure 2D:
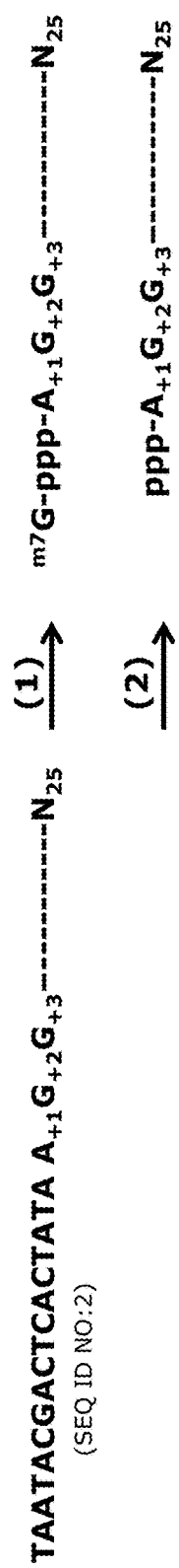

FIG. 2D shows the 5' sequence of the promoter and first 2 nucleotides of a 25 nucleotide transcript associated with a tri-nucleotide cap and a third nucleotide and the products of transcription with (1) 5' cap m$^7$G pAG and (2) 5' triphosphorylated AG.

Figure 3B:
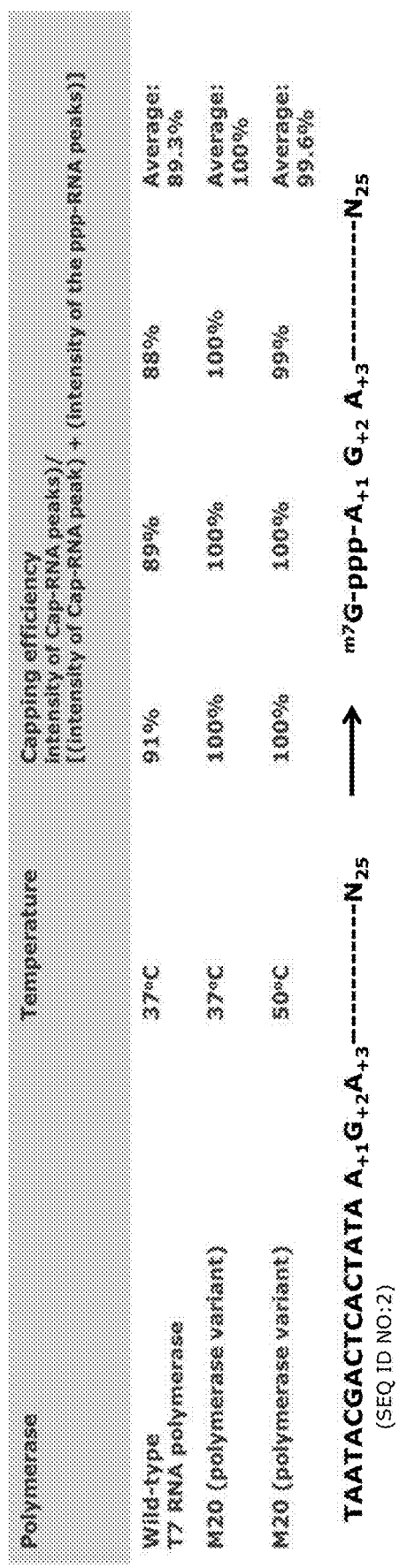
Figure 3C:
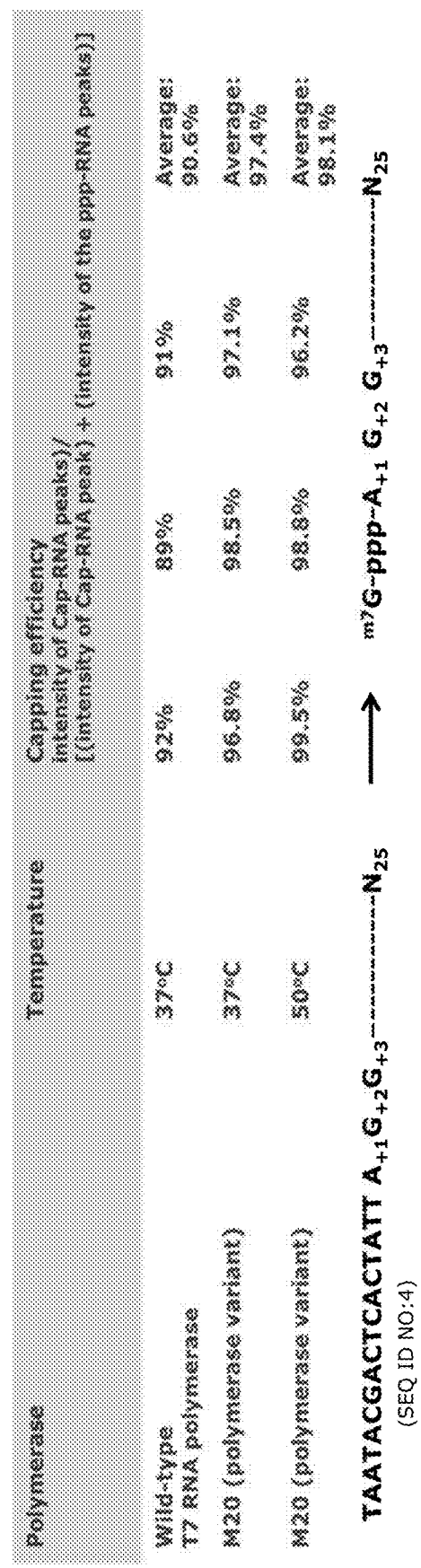

FIGS. 3A-3C provide capping efficiencies using an m$^7$G -ppp-A$_{+1}$G$_{+2}$ trinucleotide cap during transcription from templates that contained varying promoter sequences for initiation of transcription or varying the nucleotide at the +3 position on the sequence to be transcribed. The mutant M20-T7 RNA polymerase showed improved capping efficiency regardless of changes in the promoter sequence or in changes to the nucleotide at the +3 position compared with WT-T7. M20-T7 RNA polymerase has greater capping efficiency than the commercial T7 mutant RNA polymerase (Toyobo, Osaka, Japan).

The results shown in FIGS. 3A-3C demonstrate that the commercially available "Toyobo" variant of T7 RNA polymerase (Toyobo, Osaka, Japan) initiates transcription using a cap analog with less than 90% efficiency at 37° C. and 50° C. (FIG. 3A) compared with the thermostable T7 polymerase M20. Thermostable T7 RNA polymerase M20 initiates transcription using a cap analog with close to 100% efficiency at 37° C. and 50° C. (FIG. 3B). These results are consistent for the two different promoters tested (FIG. 3B and FIG. 3C).

FIG. 3A provides in tabular form, the capping efficiency comparing T7-WT RNA polymerase (37° C.) and Toyobo mutant T7 RNA polymerase (37° C. and 50° C.) for the same DNA template as FIG. 2A-2C namely a promoter sequence of TAATACGACTCACTATA (SEQ ID NO:2) with an adjacent 25 nucleotides. The transcript sequence starts at the AGG adjacent to the promoter sequence.

FIG. 3B provides the capping efficiencies observed using the same promoter sequence as in FIG. 3A but where the transcription start site for the 25 nucleotides adjacent to the promoter on the DNA template is AGA instead of AGG. The results for WT-T7 (37° C.) and M20-T7 RNA polymerase (37° C. and 50° C.) show that M20-T7 RNA polymerase transcribes this template as efficiently as the template in FIG. 3A.

FIG. 3C provides the capping efficiencies observed using a different promoter sequence from FIG. 3A and FIG. 3B namely with a promoter sequence of TAATACGACTCAC-TATT (SEQ ID NO:4) and where the adjacent 25 nucleotides of DNA template for transcription start with AGG. The results for WT-T7 (37° C.) and M20-T7 RNA polymerase (37° C. and 50° C.) show that M20-T7 RNA polymerase transcribes this template as efficiently as the template in FIGS. 3A and 3B.

FIG. 4A-4C shows that capping efficiency of a 1.7 kb functional mRNA is increased when transcription is done with the RNA polymerase variant M20. This data shows that the M20 polymerase initiates transcription of a 1.7 Kb mRNA using a cap analog with almost 100% efficiency at 37° C. and 50° C.

FIG. 4A is a schematic representation of the process involved in measuring the capping efficiency of a 1.7 kb long mRNA. The capped RNA is subjected to gel electrophoresis, RNaseH-mediated fragmentation to resolve the 5' end into capped and uncapped products and then subjected to MS analyses for evaluating the capping efficiency.

FIG. 4B Gel electrophoresis analyses of the RNase-H treated mRNA showing the presence and separation of the capped and the uncapped (ppp) 5' RNA fragments.

FIG. 4C Increased capping efficiency was observed with M20 RNA polymerase variant at 37° C. and 50° C. as compared to WT-T7 when $m^7$G-ppp-A-p-G polynucleotide cap was used in the reaction. Capping efficiency is measured using the following formula: (intensity of capped peaks)/[(intensity of capped peaks)+(intensity of the ppp peaks)].

DESCRIPTION OF EMBODIMENTS

Methods and compositions for increasing co-transcriptional capping efficiency of in vitro transcribed RNA is provided using an engineered RNA polymerase variant. Present embodiments utilize any of multiple types of polynucleotide caps as substrates for the polymerase variant for IVT of DNA templates to form capped RNA molecules.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference. Preferably, any further interpretations of terms should be consistent with U.S. Pat. No. 10,034,951.

As used herein, the term "in vitro transcription" (IVT) refers to a cell-free reaction in which a double-stranded DNA (dsDNA) template is copied by a DNA-directed RNA polymerase to produce a product that contains RNA molecules that have been copied from the template.

As used herein, the term "DNA template" refers to a dsDNA molecule that is transcribed in an IVT reaction. DNA templates have a promoter (e.g., a T7, T3 or SP6 promoter) recognized by the RNA polymerase upstream of the region that is transcribed.

As used herein, the term "RNA product" refers to the product of an IVT reaction. The RNA product of IVT contains a mixture of RNA molecules and, depending on how the transcription is done, may contain double-stranded RNA (dsRNA) molecules. The molecular events that generate dsRNA molecules in IVT reactions is unknown, but they can be detected using an antibody that is specific for dsRNA or liquid chromatography (e.g., HPLC), for example.

As used herein, the term "variant" refers to a protein that has an amino acid sequence that is different from a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence.

As used herein, the term "buffering agent", refers to an agent that allows a solution to resist changes in pH when acid or alkali is added to the solution. Examples of suitable non-naturally occurring buffering agents that may be used in the compositions, kits, and methods of the invention include, for example, Tris, HEPES, TAPS, MOPS, tricine, or MES.

The term "pharmaceutical acceptable excipient" is any solvent that is compatible with administration to a living mammalian organism via transdermal, oral, intravenous, or other administration means used in the art. Examples of pharmaceutical acceptable excipients include those described for example in U.S. 2017/0119740.

The term "non-naturally occurring" refers to a composition that does not exist in nature.

Any protein described herein may be non-naturally occurring, where the term "non-naturally occurring" refers to a protein that has an amino acid sequence and/or a post-translational modification pattern that is different from the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different from a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" protein may have one or more amino acid substitutions relative to a wild-type protein and may include a "fusion" protein. The term "fusion protein" refers to a protein composed of a plurality of polypeptide components that are unjoined in their native state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an epitope tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state.

In the context of a nucleic acid, the term "non-naturally occurring" refers to a nucleic acid that contains: a) a sequence of nucleotides that is different from a nucleic acid in its natural state (i.e., having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

The term "cap analog" refers natural caps such as $^7$mG and to a compound of the general formula R3p$_3$N1-p-N(x), where R3 is a guanine, adenine, cytosine, uridine or analogs thereof (e.g., N$^7$-methylguanosine; m$^7$G), p$_3$ is a triphosphate linkage, N1 and Nx are ribonucleosides, x is 0-8 and p is, independently for each position, a phosphate group, a phosphorothioates, phosphorodithioate, alkylphosphonate, arylphosphonate, or a N-phosphoramidate linkage. Cap analogs are added at the 5' end of an RNA transcript in a process called co-transcriptional capping to yield a 5' capped RNA (see, e.g., Muttach, supra).

Cap analogs include dinucleotide cap analogs, e.g., of formula m$^7$G(5')p3(5')G, in which a guanine nucleotide (G) is linked via its 5'OH to the triphosphate bridge. In some dinucleotide cap analogs the 3'-OH group is replaced with hydrogen or OCH$_3$ (U.S. Pat. No. 7,074,596; Kore, Nucleotides, Nucleotides, and Nucleic Acids, 2006, 25: 307-14; and Kore, Nucleotides, Nucleotides, and Nucleic Acids, 2006, 25: 337-40). Dinucleotide cap analogs include m$^7$G(5')p$_3$G, 3'-OMe-m$^7$G(5')p$_3$G (ARCA). The term "cap analog" also includes trinucleotide cap analogs (defined below) as well as other, longer, molecules (e.g., cap analog that have four, five or six or more nucleotides joined to the triphosphate bridge). In a cap analog, the 2' and 3' groups on the ribose of the m$^7$G may be independently selected O-alkyl (e.g., O-methyl), halogen, a linker, hydrogen or a hydroxyl and the sugars in N1 and NX may be independently selected from ribose, deoxyribose, 2'-O-alkyl, 2'-O-methoxyethyl, 2'-O-allyl, 2'-O-alkylamine, 2'-fluororibose, and 2'-deoxyribose. N1 and NX may independently (for each position) comprise a base selected from adenine, uridine, guanine, or cytidine or analogs of adenine, uridine, guanine, or cytidine, and nucleotide modifications can be selected from N$^6$-methyl-adenine, N$^1$-methyladenine,N$^6$-2'-O-dimethyladenosine, pseudouridine, N$^1$-methylpseudouridine, 5-iodouridine, 4-thiouridine, 2-thiouridine, 5-methyluridine, pseudoisocytosine, 5-methoxycytosine, 2-thiocytosine, 5-hydroxycytosine, N$^4$-methylcytosine, 5-hydroxymethylcytosine, hypoxanthine, N$_1$-methylguanine, O$^6$-methylguanine, 1-methyl-guanosine, N$^2$-methyl-guanosine, N$^2$,N$^2$-dimethyl-guanosine, 2-methyl-2'-O-methyl-guanosine, N$^2$,N$^2$-dimethyl-2'-O-methyl-guanosine, 1-methyl-2'-O-methyl-guanosine, N$^2$,N$^7$-dimethyl-2'-O-methyl-guanosine, and isoguanineadenine.

The term "trinucleotide cap analog" refers to a cap analog wherein x=1. Several trinucleotide cap analogs, e.g., m$^7$G (5')p$_3$ApG, m$^7$G(5')p$_3$AmpG (Am is adenine with a 2'OMe-ribose), m$^7$G(5')p$_3$ m$^6$AmpG (m$^6$A is N$^6$-methyladenine), and m$^7$G(5')p$_3$m$^6$ApG are disclosed by Ishikawa, et al., Nucleic Acid Symp. Ser., 2009 53:129-30, and many others are described in U.S. 2018/0105551, which publications are incorporated by reference herein.

Provided herein, among other things, is a method for capping an RNA in an IVT reaction, co-transcriptionally, i.e., using a cap analog. In some embodiments, the method may comprise (a) combining rNTPs, or modified rNTPs, a DNA template, a cap analog and a RNA polymerase that comprises: (i) an amino acid sequence is at least 80% sequence identity to SEQ ID NO:1; and (ii) an amino acid substitution at one or more positions corresponding to positions 388 and 567 of SEQ ID NO:1, to produce a reaction mix; and (b) incubating the reaction mix under conditions suitable for IVT of the DNA template to produce a capped RNA copy of the template. This method, in which the capping is done co-transcriptionally, results in a product that is almost completely capped (e.g., at least 90%, at least 98% or at least 99% capped) and, as such, the RNA product can potentially be used without any post-transcriptional enzymatic steps. In some embodiments the polymerase may be thermostable and, as such, the reaction can be done at a temperature that is in the range of 30° C. to 70° C., e.g., a temperature of 37° C., a temperature of 50° C. or a temperature in the range of 50° C. to 65° C.

In some embodiments, the RNA polymerase used in the method: (i) may have an amino acid sequence with at least 80% sequence identity (e.g., at least 90%, at least 90%, at least 95%, at least 97%, at least 98% or at least 99% identity) to SEQ ID NO:1; and (ii) may comprise one or more (e.g., at least two, at least three, at least five, or at least ten) amino acid substitutions at one or more positions corresponding to positions 75, 83, 108, 109, 205, 206, 227, 281, 297, 312, 323, 327, 333, 340, 354, 362, 375, 388, 428, 446, 454, 461, 495, 510, 534, 567, 584, 591, 618, 642, 711, 724, 740, 788, 832, 834, 835, 843, 847, 849, 856, 863, 866, and 877 of SEQ ID NO:1 (WT-T7), shown below:

```
SEQ ID NO: 1:
MNTINIAKNDFSDIELAAIPFNTLADHYGERLAREQLALEHESYEMGEAR

FRKMFERQLKAGEVADNAAAKPLITTLLPKMIARINDWFEEVKAKRGKRP

TAFQFLQEIKPEAVAYITIKTTLACLTSADNTTVQAVASAIGRAIEDEAR

FGRIRDLEAKHFKKNVEEQLNKRVGHVYKKAFMQVVEADMLSKGLLGGEA

WSSWHKEDSIHVGVRCIEMLIESTGMVSLHRQNAGVVGQDSETIELAPEY

AEAIATRAGALAGISPMFQPCVVPPKPWTGITGGGYWANGRRPLALVRTH

SKKALMRYEDVYMPEVYKAINIAQNTAWKINKKVLAVANVITKWKHCPVE

DIPAIEREELPMKPEDIDMNPEALTAWKRAAAAVYRKDKARKSRRISLEF

MLEQANKFANHKAIWFPYNMDWRGRVYAVSMFNPQGNDMTKGLLTLAKGK

PIGKEGYYWLKIHGANCAGVDKVPFPERIKFIEENHENIMACAKSPLENT

WWAEQDSPFCFLAFCFEYAGVQHHGLSYNCSLPLAFDGSCSGIQHFSAML

RDEVGGRAVNLLPSETVQDIYGIVAKKVNEILQADAINGTDNEVVTVTDE

NTGEISEKVKLGTKALAGQWLAYGVTRSVTKRSVMTLAYGSKEFGFRQQV

LEDTIQPAIDSGKGLMFTQPNQAAGYMAKLIWESVSVTVVAAVEAMNWLK

SAAKLLAAEVKDKKTGEILRKRCAVHWVTPDGFPVWQEYKKPIQTRLNLM

FLGQFRLQPTINTNKDSEIDAHKQESGIAPNFVHSQDGSHLRKTVVWAHE

KYGIESFALIHDSFGTIPADAANLFKAVRETMVDTYESCDVLADFYDQFA

DQLHESQLDKMPALPAKGNLNLRDILESDFAFA
```

M20 as used herein, is described by this embodiment.

In some embodiments, the RNA polymerase may comprise an amino acid substitution at one or more (e.g., at least two, three, four, five or six) positions corresponding to positions selected from 109, 205, 388, 534, 567 and 618 of SEQ ID NO:1. In some embodiments, the polymerase may comprise an amino acid substitution at one or both positions corresponding to positions 388 and 567.

In some embodiments, the RNA polymerase: (i) has an amino acid sequence with at least 80% sequence identity (e.g., at least 90%, at least 95%, at least 97%, at least 98% or at least 99% identity) to SEQ ID NO:1; and (ii) comprises one or more (e.g., at least two, at least three, at least five, or at least ten) of the following amino acid substitutions: T75Q, A83K, E108L, K206P, V227I, I281P, V297I, Y312D, A323I, A327P, K333P, V340E, A354Q, M362P, T375K, T375N, A428P, L446F, K454P, K461R, S495N, C510Q, A584K, D591E, K642R, K711R, A724P, K740R, G788A, M832F, D834E, T835L, A843Q, D847E, F849V, S856T, A863P, A866K, and E877R, wherein the amino acid substitutions are at positions that correspond to positions in SEQ ID NO:1.

In some embodiments, the variant comprises one or more (e.g., one, two, three, four, five or all six) of the following amino acid substitutions: I109L, H205S, D388E, L534V, V567P and G618Q, wherein the amino acid substitutions are at positions that correspond to positions in SEQ ID NO:1, as well as well as optionally one or more (e.g., at least two, at least three, at least five, or at least ten) of the following amino acid substitutions: T75Q, A83K, E108L, K206P, V227I, I281P, V297I, Y312D, A323I, A327P, K333P, V340E, A354Q, M362P, T375K, T375N, A428P, L446F, K454P, K461R, S495N, C510Q, A584K, D591E, K642R, K711R, A724P, K740R, G788A, M832F, D834E, T835L, A843Q, D847E, F849V, S856T, A863P, A866K, and E877R, wherein the amino acid substitutions are at positions that correspond to positions in SEQ ID NO:1

The variant RNA polymerase may contain any or all of the features described in U.S. 2017/0247670. The variant RNA polymerase may also be a variant SP6 RNA polymerase or variant T3 RNA polymerase all of which are closely related in sequence function and properties.

In one embodiment, the method for optimizing the efficiency of capping of an RNA with a cap analog includes forming a mixture of reagents with a DNA template, wherein the reagent mixture includes a mixture of rNTPs, and/or modified nucleotides, a cap analog and an RNA polymerase variant of the type described in U.S. patent application Ser. No. 15/594,090 and exemplified herein with a variant identified as M20 where M20 has at least 80% sequence identity (e.g., at least 90%, at least 95%, or 100% sequence identity) with SEQ ID NO:1, one or both mutations corresponding to position 388 and 567 in SEQ ID NO:1, and potentially other mutations up to and including any, some or all of the mutations described above. In another embodiment, at least 95% of the transcript formed in the reaction mixture is capped. In another embodiment, the efficiency of capping of a newly formed transcript using the reaction mixture is significantly greater when the RNA polymerase is mutant T7 compared with WT-T7. In another embodiment, efficiency of co-transcriptional capping is at least 95% as measured using Mass spectrometry (Mass Spec) and comparing the capped to uncapped RNA having 5'ppp.

In one embodiment, the cap analog is described in Formula 1.

Formula 1

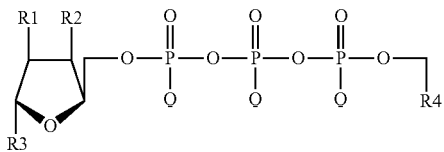

wherein:
(a) $R_1$ and $R_2$ are independently 3'-O-alkyl and/or 2'-O-alkyl e.g. alkyl=methyl, halogen or linker
(b) R3=guanine, adenine, cytosine, uridine, guanine analog, adenine analog, cytosine analog, uridine analog e.g. $m^7G$
(c) R4=$N_1$-p-N(x), where N=nucleotides or modifications thereof where the nucleotides can be selected from adenine, uridine, guanine, or cytidine or analogs of adenine, uridine, guanine, or cytidine, and nucleotide modifications can be selected from $N^6$-methyladenine, $N^1$-methyladenine,$N^6$-2'-O-dimethyladenosine, pseudouridine, $N^1$-methylpseudouridine, 5-iodouridine, 4-thiouridine, 2-thiouridine, 5-methyluridine, pseudoisocytosine, 5-methoxycytosine, 2-thiocytosine, 5-hydroxycytosine, $N^4$-methylcytosine, 5-hydroxymethylcytosine, hypoxanthine, $N_1$-methylguanine, $O^6$-methylguanine, 1-methyl-guanosine, $N^2$-methylguanosine, $N^2,N^2$-dimethyl-guanosine, 2-methyl-2'-O-methyl-guanosine, $N^2,N^2$-dimethyl-2'-O-methylguanosine, 1-methyl-2'-O-methyl-guanosine, $N^2,N^2$-dimethyl-2'-O-methyl-guanosine, or isoguanineadenine
where x can be any integer from 0-8,
wherein the sugar in the nucleotides may be selected from ribose, arabinose, threonyl furanose, thioribose, deoxyribose, and may comprise one or more modifications including 2'-O-alkyl, 2'-O-methoxyethyl, 2'-O allyl, 2'-O alkylamine, 2'-fluororibose, or 2'-deoxyribose, the phosphate groups in one or more nucleotides can be substituted for phosphorothioates, phosphorodithioate, alkyphosphonate, arylphosphonate, or N-phosphoramidate linkages.

RNA polynucleotide caps can be in a salt or solvated form. RNA polynucleotide caps can be single stereoisomers or a plurality of stereoisomers of one or more of the compounds described by Formula 1 or a salt or salts thereof.

The modified cap may include a label that can, for example, be detected by fluorescence or by color facilitating the detection and quantitation of RNA after transcription. In some embodiments the modified cap may include a binding moiety (such as biotin, desthiobiotin, digoxigenin; groups that form an irreversible bond with a protein tag (benzylguanine or benzylchoropyrimidine (SNAP-tag); benzylcytosine (CLIP-tag); haloalkane (HaloTag)) or the like to facilitate enrichment leading to for example, identification by size or mass. One or more components of the transcription reaction (initiating capped oligonucleotide primer and/or NTPs) may be labeled with a detectable label (such as anthraniloyl group, Alexa Fluor dyes; coumarin dyes, BODIPY dyes, Quantum Dots, ATTO dyes) or marker so that the RNA after can be identified, for example, by size, mass, affinity capture or color. The detectable label is a fluorescent dye; and the affinity capture label is biotin or others.

The methods and compositions provided here can be used for the in vitro synthesis by enzyme-dependent transcription of any desired DNA template and sequence to make a 5'-capped RNA. For example, the DNA template may have a sequence consistent with naturally occurring or synthetic mRNA, tRNA, guide RNA, small nuclear RNA (snRNA), small nucleolar RNA (snoRNA), small cajal body-specific RNA (scaRNA). The transcribed RNA may include one or more modified nucleoside monophosphates, one or more modified sugars in addition to the cap polynucleotide structure (Formula 1).

The cap polynucleotide can have a structure that resembles either a Cap 0 structure (no methylation of 2'OH of +1 ribose), a Cap 1 structure (methylation of 2'OH of +1 ribose), or a Cap 2 structure (methylation of 2'OH of +2 ribose) similar to natural cap structures.

While embodiments of the methods described herein describe a thermostable T7 RNA polymerase variant mediated transcription reaction, other enzymes, including natural or mutated variants that may be utilized include, for example, SP6 and T3 RNA polymerases and RNA polymerases from other sources including thermostable RNA polymerases.

Kits including, the cap analog and the polymerase variant for performing transcription are also contemplated with one or more of the following reagents: modified or unmodified cap analog, one or more unmodified NTPs, one or more modified NTPs, an RNA polymerase or variant, other enzymes, a reaction buffer, magnesium and a DNA template. In some embodiments, the RNA product may encode a protein, e.g., a therapeutic protein or a protein expected to alter the cells into which it is introduced and, as such, the RNA molecules in the RNA product may have a 5' untranslated region (5' UTR), one or more coding sequences, and a 3' translated region (3' UTR), where the 3' and 5' UTRs facilitate translation of the one or more coding sequence to produce a protein within the cells. In other embodiments, the RNA product may be a therapeutic RNA. In some embodiments the RNA product may be a guide RNA, a short hairpin RNA, a siRNA, a microRNA, a long noncoding RNA, or a protein-coding RNA (which may encode a recombinant protein or a protein that is native to the cells). In some embodiments, the RNA product may contain modified nucleotides (triphosphates for which can be added to the IVT reaction).

In these embodiments, modified nucleotides may be incorporated into the IVT RNA. Incorporation of modified nucleotides can increase in translation efficiency of the RNA and increased stability of the RNA.

Modifications can be present either in the sugars (e.g., 2'-fluororibose, ribose, 2'-deoxyribose, arabinose, and hexose); and/or in the phosphate groups (e.g., phosphorothioates and 5'-N-phosphoramidite linkages); and/or in the nucleotide base (for example, see: U.S. Pat. No. 8,383,340; WO 2013/151666; U.S. Pat. No. 9,428,535 B2; U.S. 2016/0032316). In some embodiments, the RNA product may be altered during or after the transcription reaction, e.g., to decrease the rate at which the RNA products are degraded in the cells. In some embodiment, the RNA product may contain capped RNAs (see, for example: WO 2016/090262; WO 2014/152673; WO 2009/149253; Strenkowska, et al., (2016), Nucleic Acids Research, 44(20):9578-90). RNAs with poly A tails of varying length and labeled RNAs can also be produced.

In some embodiments, the method may further comprise testing or using the RNA product (e.g., administering the RNA to a mammalian cell that in vitro (i.e., grown in culture), ex vivo or in vivo, without performing post-transcriptional enzymatic step that removes ppp-G and adds a $m^7$G-ppp to the 5' end of the RNA product.

In any embodiment, the IVT may be done using natural NTPs, i.e., GTP, CTP, UTP and ATP to produce a product that does not contain modified nucleosides.

In any embodiment, the IVT may be done using NTPs corresponding to G, C, U and A in the absence of pseudo-uridine triphosphate to produce a product that does not contain pseudo-uridine. The cells into which the RNA product is introduced may be in vitro (i.e., cells that have been cultured in vitro on a synthetic medium). In these embodiments, the RNA product may be transfected into the cells. In other embodiments, the cells into which the RNA product is introduced may be in vivo (cells that are part of a mammal). In these embodiments, the introducing may be done by administering the RNA product to a subject in vivo. In some embodiments, the cells into which the RNA product is introduced may present ex vivo (cells that are part of a tissue, e.g., a soft tissue that has been removed from a mammal or isolated from the blood of a mammal).

Methods for making a formulation are also provided. In some embodiments, the method may comprise combining an RNA product made by transcribing a template DNA as described above with a pharmaceutically acceptable excipient to produce a formulation.

In some embodiments, the method comprises (a) transcribing a template DNA with the RNA polymerase using the method described above to produce a capped RNA product with or without modifications; and (b) combining the RNA product with a pharmaceutically acceptable excipient; wherein the method is done in the absence of a post-transcriptional capping step.

In some embodiments, the method may include administering the formulation to a mammalian subject in an effective therapeutic dose, where the subject may be a human or any non-human animal (e.g., mouse, rat, rabbit, dog, cat, cattle, swine, sheep, horse or primate). Alternatively, the capped RNA may be administered to non-mammalian subject or eukaryotic or prokaryotic cells in vivo or in vivo.

The capped RNA can either be naked or formulated with a suitable excipient for administration to a subject, e.g., a human. Formulations can include liquid formulations (solutions, suspensions, dispersions), topical formulations (gels, ointments, drops, creams), liposomal formulations (such as those described in: U.S. Pat. No. 9,629,804 B2; U.S. 2012/0251618 A1; WO 2014/152211; U.S. 2016/0038432 A1). The formulations may include encapsulating the RNA in virus particles.

In some embodiments, capped RNA product can be delivered into the cells by packaging them into nanoparticles such as cationic lipids and polymers, non-viral carriers like protamine. Direct introduction of the RNA into the cell using transfection, microinjection, electroporation, sonoporation can also be implemented. The delivery (localized or systemic) and the packaging of the RNA (with or without modifications) can be performed at temperatures optimal for the delivery approach or the formulation used (such as those described in: U.S. Pat. No. 9,629,804 B2; U.S. 2012/0251618 A1; WO 2014/152211; U.S. 2016/0038432 A1; U.S. 2016/0032316 A1; U.S. Pat. No. 9,597,413 B2; U.S. 2012/0258176).

The methods and compositions provided here can be used for the in vitro synthesis of capped RNA products encoding proteins such as antigens for vaccines, for cancer immunotherapies (such as those described in: U.S. Pat. No. 8,217,016 B2; U.S. 2012/0009221 A1; U.S. 2013/0202645 A1; U.S. Pat. No. 9,587,003 B2; Sahin et. al., (2014): Nature Reviews Drug Discovery 13, 759-80), or allergy tolerance (such as those described in Sahin (2014), supra), or for producing recombinant or naturally occurring protein for protein replacement therapeutics (such as those described in: U.S. 2016/0032316 A1; U.S. Pat. No. 8,680,069; PCT/US2013/031821; PCT/US2014/028330; U.S. Pat. No. 9,181,321; U.S. Pat. No. 9,220,792 B2; U.S. Pat. No. 9,233,141 B2; Sahin (2014), supra), supplementation therapeutics (such as those described in Sahin (2014), supra), cell reprogramming (such as those described in: U.S. 2011/0143436 A1; U.S. Pat. No. 8,802,438; U.S. Pat. No. 9,371,544; WO 2009/077134 A2; Sahin (2014), supra), genome editing/engineering (such as those described in Sahin (2014), supra). Introduction of capped RNA into target cells can change the cell phenotype by production of proteins or by affecting expression of targets in the cell.

All references cited herein are incorporated by reference.

EMBODIMENTS

Embodiment 1. A method for capping an RNA in an IVT reaction, comprising:
(a) combining rNTPs, a DNA template, a cap analog and a RNA polymerase that comprises: (i) an amino acid sequence that is at least 80% sequence identical to SEQ ID NO:1; and (ii) an amino acid substitution at one or more positions corresponding to positions 388 and 567 of SEQ ID NO:1, to produce a reaction mix; and
(b) incubating the reaction mix under conditions suitable for IVT of the DNA template to produce a capped RNA copy of the template.

Embodiment 2. The method of embodiment 1, wherein the cap analog is a dinucleotide cap analog.

Embodiment 3. The method of embodiment 1, wherein the cap analog is a trinucleotide cap analog.

Embodiment 4. The method of any prior embodiment, wherein the cap analog is of the formula R3 p3-$N_1$-p-N(x), wherein:
$m^7G$ is a N7-methylguanine ribonucleoside;
p3 is a triphosphate linkage;
p is, independently for each position, a phosphate group, a phosphorothioate, phosphorodithioate, alkylphosphonate, arylphosphonate, or an N-phosphoramidate linkage;
N1 and Nx are ribonucleosides; and
x is 0-8 (e.g. X is 1 or 2).

Embodiment 5. The method of embodiment 4, wherein the 2' and 3' groups on the ribose of the $m^7G$ are independently selected O-alkyl (O-methyl), halogen, a linker, hydrogen or a hydroxyl.

Embodiment 6. The method of embodiment 4 or 5, wherein the sugars in N1 and Nx (e.g. x=1, 2 or 3) are independently for each position selected from ribose, deoxyribose, and may comprise of modifications including 2'-O-alkyl, 2'-O-methoxyethyl, 2'-O allyl, 2'-O alkylamine, 2'-fluororibose, and 2'-deoxyribose.

Embodiment 7. The method of any of embodiments 4-6, wherein the bases in N1 and Nx (e.g. where x=1, 2 or 3) are independently for each position selected from adenine, uridine, guanine, or cytidine or analogs of adenine, uridine, guanine, or cytidine, and nucleotide modifications can be selected from N6-methyladenine, N1-methyladenine, N6-2'-O-dimethyladenosine, pseudouridine, N1-methylpseudouridine, 5-iodouridine, 4-thiouridine, 2-thiouridine, 5-methyluridine, pseudoisocytosine, 5-methoxycytosine, 2-thiocytosine, 5-hydroxycytosine, N4-methylcytosine, 5-hydroxymethylcytosine, hypoxanthine, N1-methylguanine, O6-methylguanine, 1-methyl-guanosine, N2-methyl-guanosine, N2,N2-dimethyl-guanosine, 2-methyl-2'-O-methyl-guanosine, N2,N2-dimethyl-2'-O-methyl-guanosine, 1-methyl-2'-O-methyl-guanosine, N2,N7-dimethyl-2'-O-methyl-guanosine, and isoguanineadenine.

Embodiment 8. The method of any prior embodiment, wherein the RNA polymerase comprises an amino acid substitution at positions corresponding to positions 388 and 567 of SEQ ID NO:1.

Embodiment 9. The method of any prior embodiment, wherein the RNA polymerase further comprises an amino acid substitution of at least one position corresponding to positions selected from 109, 205, 534, and 618 of SEQ ID NO:1.

Embodiment 10. The method of any prior embodiment, wherein the RNA polymerase further comprises an amino acid substitution of at least three two positions corresponding to positions selected from 109, 205, 534 and 618 of SEQ ID NO:1.

Embodiment 11. The method of any prior embodiment, wherein the RNA polymerase further comprises an amino acid substitution at positions corresponding to positions 109, 205, 534 and 618 of SEQ ID NO:1.

Embodiment 12. A kit comprising:
(a) a cap analog; and
(b) an RNA polymerase that comprises: (i) an amino acid sequence is at least 80% sequence identity to SEQ ID NO:1; and (ii) an amino acid substitution at one or more positions corresponding to positions 388 and 567 of SEQ ID NO:1.

Embodiment 13. The kit of embodiment 12, wherein the cap analog is a dinucleotide cap analog.

Embodiment 14. The kit of embodiment 12, wherein the cap analog is a trinucleotide cap analog.

Embodiment 15. The kit of any of claims 10-12, wherein the cap analog is of the formula R3p3-N1-p-Nx, wherein
$m^7G$ is an N7-methylguanine ribonucleoside;
p3 is a triphosphate linkage;
p is a phosphate;
N1 and NX are ribonucleosides;
x is 0-8 (e.g. X is 1 or 2); and
p is, independently for each position, a phosphate group, a phosphorothioates, phosphorodithioate, alkylphosphonate, arylphosphonate, or a N-phosphoramidate linkage.

Embodiment 16. The method of embodiment 15, wherein the 2' and 3' groups on the ribose of the $m^7G$ are independently selected O-alkyl (O-methyl), halogen, a linker, hydrogen or a hydroxyl.

Embodiment 17. The kit of embodiment 15 or 16, wherein the sugars in N1 and NX are independently selected from ribose, deoxyribose, and comprise of modifications including 2'-O-alkyl, 2'-O-methoxyethyl, 2'-O allyl, 2'-O alkylamine, 2'-fluororibose, and 2'-deoxyribose.

Embodiment 18. The kit of any of embodiments 15-17, wherein the bases in N1 and NX are be independently for each position selected from adenine, uridine, guanine, or cytidine or analogs of adenine, uridine, guanine, or cytidine, and nucleotide modifications can be selected from N6-methyladenine, N1-methyladenine, N6-2'-O-dimethyladenosine, pseudouridine, N1-methylpseudouridine, 5-iodouridine, 4-thiouridine, 2-thiouridine, 5-methyluridine, pseudoisocytosine, 5-methoxycytosine, 2-thiocytosine, 5-hydroxycytosine, N4-methylcytosine, 5-hydroxymethylcytosine, hypoxanthine, N1-methylguanine, O6-methylguanine, 1-methyl-guanosine, N2-methyl-guanosine, N2,N2-dimethyl-guanosine, 2-methyl-2'-O-methyl-guanosine, N2,N2-dimethyl-2'-O-methyl-guanosine, 1-methyl-2'-O-methyl-guanosine, N2,N7-dimethyl-2'-O-methyl-guanosine, and isoguanineadenine.

Embodiment 19. The kit of any of embodiments 12-18, wherein the RNA polymerase comprises an amino acid substitution at positions corresponding to positions 388 and 567 of SEQ ID NO:1.

Embodiment 20. The kit of any of embodiments 12-19, wherein the RNA polymerase further comprises an amino acid substitution of at least one position corresponding to positions selected from 109, 205, 534, and 618 of SEQ ID NO:1.

Embodiment 21. The kit of any of embodiments 12-20, wherein the RNA polymerase further comprises an amino acid substitution of at least three two positions corresponding to positions selected from 109, 205, 534 and 618 of SEQ ID NO:1.

Embodiment 22. The kit of any of embodiments 12-21, wherein the RNA polymerase further comprises an amino acid substitution at positions corresponding to positions 109, 205, 534 and 618 of SEQ ID NO:1.

Embodiment 23. A method for capping an RNA in an IVT reaction, comprising:
(a) combining rNTPs, a DNA template, a trinucleotide cap analog and a RNA polymerase that comprises:
(i) an amino acid sequence is at least 95% sequence identity to SEQ ID NO:1; and (ii) an amino acid substitution at one or more positions corresponding to positions 388 and 567 of SEQ ID NO:1, to produce a reaction mix; and
(b) incubating the reaction mix under conditions suitable for IVT of the DNA template to produce a capped RNA copy of the template.

Embodiment 24. The method of embodiment 23, wherein the trinucleotide cap analog is of the formula
m$^7$G p3N1-p-Nx, wherein:
m$^7$G is a N7-methylguanine ribonucleoside;
p3 is a triphosphate linkage;
p is a phosphate;
x=1; and
N1 and Nx are independently ribonucleosides.

Embodiment 25. The method of embodiment 24, wherein N1 and Nx independently for each position comprise a base selected from adenine, uridine, guanine, or cytidine or analogs of adenine, uridine, guanine, or cytidine, and nucleotide modifications can be selected from N6-methyladenine, N1-methyladenine,N6-2'-O-dimethyladenosine, pseudouridine, N1-methylpseudouridine, 5-iodouridine, 4-thiouridine, 2-thiouridine, 5-methyluridine, pseudoisocytosine, 5-methoxycytosine, 2-thiocytosine, 5-hydroxycytosine, N4-methylcytosine, 5-hydroxymethylcytosine, hypoxanthine, N1-methylguanine, O6-methylguanine, 1-methylguanosine, N2-methyl-guanosine, N2,N2-dimethylguanosine, 2-methyl-2'-O-methyl-guanosine, N2,N2-dimethyl-2'-O-methyl-guanosine, 1-methyl-2'-O-methyl-guanosine, N2,N7-dimethyl-2'-O-methyl-guanosine, or isoguanineadenine.

Embodiment 26. The method of embodiment 24 or 25, wherein the 2' and 3' positions of the ribose of the m$^7$G are hydroxyls.

Embodiment 27. The method of embodiment 24 or 25, wherein the 3' position of the ribose of the m$^7$G is a hydroxyl and the 3' position of the ribose of the m$^7$G is an O-alkyl, halogen, a linker, hydrogen or a hydroxyl.

Embodiment 28. The method of any of embodiments 23-27, wherein the RNA polymerase comprises an amino acid substitution at positions corresponding to positions 388 and 567 of SEQ ID NO:1.

Embodiment 29. The method of any of embodiments 23-28, wherein the RNA polymerase further comprises an amino acid substitution of at least one position corresponding to positions selected from 109, 205, 534, and 618 of SEQ ID NO:1.

Embodiment 30. The method of any of embodiments 23-29, wherein the RNA polymerase further comprises an amino acid substitution of at least three two positions corresponding to positions selected from 109, 205, 534 and 618 of SEQ ID NO:1.

Embodiment 31. The method of any of embodiments 23-30, wherein the RNA polymerase further comprises an amino acid substitution at positions corresponding to positions 109, 205, 534 and 618 of SEQ ID NO:1.

Embodiment 32. A kit comprising:
(a) a trinucleotide cap analog; and
(b) a RNA polymerase that comprises: (i) an amino acid sequence is at least 95% sequence identity to SEQ ID NO:1; and (ii) an amino acid substitution at one or more positions corresponding to positions 388 and 567 of SEQ ID NO:1.

Embodiment 33. The kit of embodiment 32, further comprising rNTPs.

Embodiment 34. The kit of embodiment 23 or 33, wherein the trinucleotide cap analog is of the formula m$^7$G p3N1-p-Nx, wherein:
m$^7$G is a N7-methylguanine ribonucleoside;
p3 is a triphosphate linkage;
p is a phosphate;
x=1; and
N1 and NX are independently ribonucleosides.

Embodiment 35. The kit of embodiment 34, wherein N1 and Nx independently for each position comprise a base selected from adenine, uridine, guanine, or cytidine or analogs of adenine, uridine, guanine, or cytidine, and nucleotide modifications can be selected from N6-methyladenine, N1-methyladenine,N6-2'-O-dimethyladenosine, pseudouridine, N1-methylpseudouridine, 5-iodouridine, 4-thiouridine, 2-thiouridine, 5-methyluridine, pseudoisocytosine, 5-methoxycytosine, 2-thiocytosine, 5-hydroxycytosine, N4-methylcytosine, 5-hydroxymethylcytosine, hypoxanthine, N1-methylguanine, O6-methylguanine, 1-methylguanosine, N2-methyl-guanosine, N2,N2-dimethylguanosine, 2-methyl-2'-O-methyl-guanosine, N2, N2-dimethyl-2'-O-methyl-guanosine, 1-methyl-2'-O-methyl-guanosine, N2,N7-dimethyl-2'-O-methyl-guanosine, or isoguanineadenine.

Embodiment 36. The kit of embodiment 34 or 35, wherein the 2' and 3' positions of the ribose of the m$^7$G are hydroxyls.

Embodiment 37. The kit of any of embodiments 34-36, wherein the 3' position of the ribose of the m$^7$G is a hydroxyl and the 3' position of the ribose of the m$^7$G is an O-alkyl, halogen, a linker, hydrogen or a hydroxyl.

Embodiment 38. The kit of any of embodiments 34-37, wherein the RNA polymerase comprises an amino acid substitution at positions corresponding to positions 388 and 567 of SEQ ID NO:1.

Embodiment 39. The kit of any of embodiments 34-38, wherein the RNA polymerase further comprises an amino acid substitution of at least one position corresponding to positions selected from 109, 205, 534, and 618 of SEQ ID NO:1.

Embodiment 40. The kit of any of embodiments 34-39, wherein the RNA polymerase further comprises an amino acid substitution of at least three two positions corresponding to positions selected from 109, 205, 534 and 618 of SEQ ID NO:1.

Embodiment 41. The kit of any of embodiments 34-40, wherein the RNA polymerase further comprises an amino acid substitution at positions corresponding to positions 109, 205, 534 and 618 of SEQ ID NO:1.

EXAMPLES

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. To exemplify the claimed invention, figures have been provided and described in some detail above. The results they demonstrate may be achieved using the methods described below.

Example 1

Method for Capping RNA Transcripts

IVT and Synthesis of IVT RNA Controls (Absent Caps)

IVT reactions were performed according to the description provided by New England Biolabs, Ipswich, MA, catalog 2017/2018 with WT-T7 and with T7 RNA polymerase from Toyobo using the optimized protocol from Toyobo and T7 RNA variants (M20) using the protocol described for WT-T7 RNA polymerase (New England Biolabs Inc, Ipswich, Mass.). The double stranded DNA templates for FIG. 1, 2A-2D and 3A-3C were generated by annealing two single-stranded DNA oligonucleotides. The DNA template for FIG. 4A-C was double stranded plasmid DNA linearized using restriction endonuclease NotI at a site downstream of the T7 promoter (New England Biolabs Inc, Ipswich, Mass.). Reactions were performed at 37° C. or 50° C. for 1 hour. The RNA products of IVT RNAs were processed through a spin column (Norgen Biotek Corp., Ontario, or MEGACLEAR™, Thermo Fisher Scientific, Waltham, Mass.) to remove unincorporated nucleotides before mass-spectrometry analyses.

IVT and Synthesis of IVT RNA Controls (with Caps by Co-Transcriptional Capping)

Using the same method as above, 4mM of the trinucleotide cap ($m^7G$ -ppp-A-p-G) was used for each reaction according to methods described by Trilink Biotechnologies, CA.

Assay for Measuring Capping Efficiency using LC-Mass Spectrometry

The spin column processed RNA was subjected to liquid chromatography mass spectroscopy (LC-MS) analyses (Novatia LLC, PA). The capping efficiency was determined using the following formula (intensity of capped peaks)/[(intensity of capped peak)+(intensity of the ppp peak)].

Assay for Measuring Capping Efficiency of Long mRNAs

In vitro transcribed mRNAs were generated with RNA polymerase variants in presence of trinucleotide caps (Trilink BioTechnologies, San Diego, Calif.) were processed through a spin column (MEGACLEAR™, Thermo Fisher Scientific, Waltham, Mass.) to remove unincorporated nucleotides. A 25mer oligonucleotide whose sequence is complementary to the 5' end of the transcribed capped RNA was annealed to the RNA and the annealed oligonucleotide-RNA hybrid was then subjected to RNaseH (New England Biolabs Inc, Ipswich, Mass.) digestion. The reaction products were then separated by gel electrophoresis so that the 25mer double stranded capped RNA was detected in one band on the gel and the uncapped products were observed in a second band as shown in FIG. 4B. The nucleic acid in both bands were separately extracted and subjected to liquid chromatography mass spectroscopy (LC-MS) analyses. Capping efficiency was determined using the following formula (intensity of capped peaks)/[(intensity of capped peak)+(intensity of the ppp peak)].

What is claimed is:

1. A method for capping an RNA with a cap analog, comprising:
   (a) combining in a mixture,
      ribonucleotide triphosphates (rNTPs) and/or modifications thereof,
      a cap analog, and
      an RNA polymerase, wherein the RNA polymerase: (i) has at least 90% sequence identity to SEQ ID NO: 1; and (ii) comprises an amino acid substitution at the position corresponding to position 388 and at the position corresponding to position 567 of SEQ ID NO: 1,
   (b) co-transcriptionally capping the RNA to produce capped RNA with an efficiency of co-transcriptional capping of at least 95% as measured using mass spectrometry and comparing the capped RNA to uncapped RNA having a 5'ppp.

2. The method according to claim 1, wherein the RNA polymerase further comprises an amino acid substitution of at least one position corresponding to positions selected from the group consisting of: 109, 205, 534, and 618 of SEQ ID NO:1.

3. The method according to claim 1, wherein the RNA polymerase further comprises an amino acid substitution of at least two positions corresponding to positions selected from the group consisting of: 109, 205, 534, and 618 of SEQ ID NO:1.

4. The method according to claim 1, wherein the RNA polymerase further comprises an amino acid substitution at four positions corresponding to positions 109, 205, 534, and 618 of SEQ ID NO:1.

5. The method according to claim 1, wherein the amino acid substitutions at positions corresponding to positions 388 and 567 of SEQ ID NO:1 are D388E and V567P.

6. The method according to claim 1, wherein the RNA polymerase further comprises an amino acid substitution at one or more positions corresponding to positions selected from the group consisting of: 75, 83, 108, 206, 227, 281, 297, 312, 323, 327, 333, 340, 354, 362, 375, 428, 446, 454, 461, 495, 510, 584, 591, 642, 711, 724, 740, 788, 832, 834, 835, 843, 847, 849, 856, 863, 866 and 877 of SEQ ID NO:1.

7. The method according to claim 1, wherein the RNA polymerase further comprises at least 10 of the following amino acid substitutions corresponding to positions selected from the group consisting of: 75, 83, 108, 206, 227, 281, 297, 312, 323, 327, 333, 340, 354, 362, 375, 428, 446, 454, 461, 495, 510, 584, 591, 642, 711, 724, 740, 788, 832, 834, 835, 843, 847, 849, 856, 863, 866 and 877 of SEQ ID NO:1.

8. The method according to claim 1, wherein the RNA polymerase further comprises one or more of the following amino acid substitutions selected from the group consisting of: T75Q, A83K, E108L, K206P, V227I, I281P, V297I, Y312D, A323I, A327P, K333P, V340E, A354Q, M362P, T375K, T375N, A428P, L446F, K454P, K461R, S495N, C510Q, A584K, D591E, K642R, K711R, A724P, K740R, G788A, M832F, D834E, T835L, A843Q, D847E, F849V, S856T, A863P, A866K and E877R, wherein the amino acid substitutions are at positions that correspond to positions in SEQ ID NO:1.

9. The method according to claim 1, wherein the RNA polymerase further comprises at least 10 of the following acid substitutions selected from the group consisting of: T75Q, A83K, E108L, K206P, V227I, I281P, V297I, Y312D, A323I, A327P, K333P, V340E, A354Q, M362P, T375K, T375N, A428P, L446F, K454P, K461R, S495N, C510Q, A584K, D591E, K642R, K711R, A724P, K740R, G788A, M832F, D834E, T835L, A843Q, D847E, F849V, S856T, A863P, A866K and E877R wherein the amino acid substitutions are at positions that correspond to positions in SEQ ID NO:1.

10. The method according to claim 1, wherein the RNA polymerase comprises a fusion to an exogenous DNA binding domain.

11. The method according to claim 1, wherein the cap analog comprises Formula 1, wherein Formula 1, comprises:

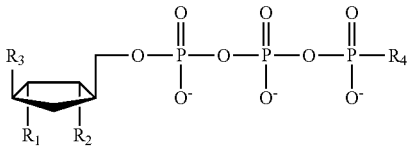

$R_1$ and/or $R_2$=O-alkyl, halogen, a linker, hydrogen or a hydroxyl;
$R_3$=guanine, adenine, cytosine, uridine, guanine analog, adenine analog, cytosine analog, or uridine analog;
$R_4$=$N_1$(p–Nx) where N is a nucleoside or a modified nucleoside where the nucleoside is selected from adenine, uridine, guanine, or cytidine or analogs of adenine, uridine, guanine, or cytidine, and the modified nucleoside is selected from $N^6$-methyladenine, $N^1$-methyladenine,$N^6$-2'-O-dimethyladenosine, pseudouridine, $N^1$-methylpseudouridine, 5-iodouridine, 4-thiouridine, 2-thiouridine, 5-methyluridine, pseudoisocytosine, 5-methoxycytosine, 2-thiocytosine, 5-hydroxycytosine, $N^4$-methylcytosine, 5-hydroxymethylcytosine, hypoxanthine, $N_1$-methylguanine, $O^6$-methylguanine, 1-methyl-guanosine, $N^2$-methylguanosine ($m^2G$), $N^2,N^2$-dimethyl-guanosine ($m^{2,2}G$), 2-methyl-2'-O-methyl-guanosine ($m^2Gm$), $N^2,N^2$-dimethyl-2'-O-methyl-guanosine ($m^{2,2}Gm$) 1-methyl-2'-O-methyl-guanosine, $N^2,N^7$-dimethyl-2'-O-methyl-guanosine ($m^{2,7}Gm$), or isoguanineadenine wherein:

(i) x can be any integer from 0-8,
  wherein the sugar in the nucleotides may be selected from ribose, deoxyribose, and comprise of modifications including 2'-O-alkyl, 2'-O-methoxyethyl, 2'-O allyl, 2'-O alkylamine, 2'-fluororibose, or 2'-deoxyribose;
  the phosphate groups in one or more nucleotides can be substituted for phosphorothioates, phosphorodithioate, alkylphosphonate, arylphosphonate, or N-phosphoramidate linkages;
(ii) the polynucleotide cap can be a salt or solvated form; and
(iii) the polynucleotide cap can be a single stereoisomer or plurality of stereoisomers of one or more of the compounds described by Formula 1 or a salt or salts thereof.

12. The method according to claim 11, wherein the O-alkyl is an O-methyl.

13. The method according to claim 11, wherein x is 1.

14. The method according to claim 13, wherein R3 is 7 methylguanine, R1 and R2 are hydroxyl groups.

15. The method according to claim 13, wherein R3 is 7 methylguanine, R1 and R2 are O-alkyl.

16. The method according to claim 1, wherein the mixture further comprises a nucleic acid template.

17. The method according to claim 1, wherein the mixture further comprises a DNA template.

18. The method according to claim 1, wherein the co-transcriptionally capping further comprises co-transcriptionally capping the RNA at a temperature that is in the range of 30° C. to 70° C.

19. The method according to claim 1, wherein the co-transcriptionally capping further comprises co-transcriptionally capping the RNA at a temperature that is in the range of 50° C. to 65° C.

20. The method according to claim 1, wherein the ribonucleotide triphosphates (rNTPs) and/or modifications thereof further comprises at least one unmodified ribonucleotide triphosphate and at least one modified ribonucleotide triphosphate, wherein the at least one modified ribonucleotide optionally comprises a modification in its sugar group, its phosphate group, and/or its base.

* * * * *

SEQUENCE LISTING

<160> NUMBER OF SEQ ID NOS: 4

<210> SEQ ID NO 1
<211> LENGTH: 883
<212> TYPE: PRT
<213> ORGANISM: Artificial Sequence
<220> FEATURE:
<223> OTHER INFORMATION: Synthetic construct

<400> SEQUENCE: 1

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160
```

```
His Phe Lys Lys Asn Val Glu Glu Gln Leu Asn Lys Arg Val Gly His
                165                 170                 175
Val Tyr Lys Lys Ala Phe Met Gln Val Val Glu Ala Asp Met Leu Ser
                180                 185                 190
Lys Gly Leu Leu Gly Gly Glu Ala Trp Ser Ser Trp His Lys Glu Asp
            195                 200                 205
Ser Ile His Val Gly Val Arg Cys Ile Glu Met Leu Ile Glu Ser Thr
        210                 215                 220
Gly Met Val Ser Leu His Arg Gln Asn Ala Gly Val Val Gly Gln Asp
225                 230                 235                 240
Ser Glu Thr Ile Glu Leu Ala Pro Glu Tyr Ala Glu Ala Ile Ala Thr
                245                 250                 255
Arg Ala Gly Ala Leu Ala Gly Ile Ser Pro Met Phe Gln Pro Cys Val
                260                 265                 270
Val Pro Pro Lys Pro Trp Thr Gly Ile Thr Gly Gly Tyr Trp Ala
            275                 280                 285
Asn Gly Arg Arg Pro Leu Ala Leu Val Arg Thr His Ser Lys Lys Ala
        290                 295                 300
Leu Met Arg Tyr Glu Asp Val Tyr Met Pro Glu Val Tyr Lys Ala Ile
305                 310                 315                 320
Asn Ile Ala Gln Asn Thr Ala Trp Lys Ile Asn Lys Lys Val Leu Ala
                325                 330                 335
Val Ala Asn Val Ile Thr Lys Trp Lys His Cys Pro Val Glu Asp Ile
                340                 345                 350
Pro Ala Ile Glu Arg Glu Glu Leu Pro Met Lys Pro Glu Asp Ile Asp
            355                 360                 365
Met Asn Pro Glu Ala Leu Thr Ala Trp Lys Arg Ala Ala Ala Val
        370                 375                 380
Tyr Arg Lys Asp Lys Ala Arg Lys Ser Arg Ile Ser Leu Glu Phe
385                 390                 395                 400
Met Leu Glu Gln Ala Asn Lys Phe Ala Asn His Lys Ala Ile Trp Phe
                405                 410                 415
Pro Tyr Asn Met Asp Trp Arg Gly Arg Val Tyr Ala Val Ser Met Phe
            420                 425                 430
Asn Pro Gln Gly Asn Asp Met Thr Lys Gly Leu Leu Thr Leu Ala Lys
        435                 440                 445
Gly Lys Pro Ile Gly Lys Glu Gly Tyr Tyr Trp Leu Lys Ile His Gly
    450                 455                 460
Ala Asn Cys Ala Gly Val Asp Lys Val Pro Phe Pro Glu Arg Ile Lys
465                 470                 475                 480
Phe Ile Glu Glu Asn His Glu Asn Ile Met Ala Cys Ala Lys Ser Pro
                485                 490                 495
Leu Glu Asn Thr Trp Trp Ala Glu Gln Asp Ser Pro Phe Cys Phe Leu
            500                 505                 510
Ala Phe Cys Phe Glu Tyr Ala Gly Val Gln His His Gly Leu Ser Tyr
        515                 520                 525
Asn Cys Ser Leu Pro Leu Ala Phe Asp Gly Ser Cys Ser Gly Ile Gln
    530                 535                 540
His Phe Ser Ala Met Leu Arg Asp Glu Val Gly Gly Arg Ala Val Asn
545                 550                 555                 560
Leu Leu Pro Ser Glu Thr Val Gln Asp Ile Tyr Gly Ile Val Ala Lys
                565                 570                 575
```

-continued

```
Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
        610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
        690                 695                 700

Leu Leu Ala Ala Glu Val Lys Asp Lys Thr Gly Glu Ile Leu Arg
705                 710                 715                 720

Lys Arg Cys Ala Val His Trp Val Thr Pro Asp Gly Phe Pro Val Trp
                725                 730                 735

Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
        770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 2
<211> LENGTH: 17
<212> TYPE: DNA
<213> ORGANISM: Artificial Sequence
<220> FEATURE:
<223> OTHER INFORMATION: Synthetic construct

<400> SEQUENCE: 2
taatacgact cactata                                                  17

<210> SEQ ID NO 3
<211> LENGTH: 17
<212> TYPE: DNA
<213> ORGANISM: Artificial Sequence
<220> FEATURE:
<223> OTHER INFORMATION: Synthetic construct
```

```
<400> SEQUENCE: 3
attatgctga gtgatat                                                  17

<210> SEQ ID NO 4
<211> LENGTH: 17
<212> TYPE: DNA
<213> ORGANISM: Artificial Sequence
<220> FEATURE:
<223> OTHER INFORMATION: Synthetic construct

<400> SEQUENCE: 4
taatacgact cactatt                                                  17
```